United States Patent [19]

Wick

[11] Patent Number: 4,751,087

[45] Date of Patent: Jun. 14, 1988

[54] TRANSDERMAL NITROGLYCERIN DELIVERY SYSTEM

[75] Inventor: Steven M. Wick, Oakdale, Minn.

[73] Assignee: Riker Laboratories, Inc., St. Paul, Minn.

[21] Appl. No.: 725,215

[22] Filed: Apr. 19, 1985

[51] Int. Cl.⁴ .................. A61F 13/00; A61K 9/70
[52] U.S. Cl. ....................... 424/449; 424/78; 424/81; 424/448; 514/509; 604/896; 604/897
[58] Field of Search ............ 424/16, 21, 28, 32, 424/78, 81, 449; 514/509; 604/896, 897; 128/156

[56] References Cited

U.S. PATENT DOCUMENTS

| | | | |
|---|---|---|---|
| 3,742,951 | 7/1973 | Zaffaroni | 128/268 |
| 4,409,206 | 10/1983 | Stricker | 424/28 |
| 4,485,087 | 11/1984 | Otsuka et al. | 424/28 |
| 4,542,013 | 9/1985 | Keith | 424/28 |
| 4,585,452 | 4/1986 | Sablotsky | 604/896 |
| 4,588,580 | 5/1986 | Gale et al. | 424/21 |

FOREIGN PATENT DOCUMENTS

| | | |
|---|---|---|
| 0062682 | 10/1982 | European Pat. Off. |
| WO86/00814 | 2/1986 | PCT Int'l Appl. |
| 1518683 | 7/1978 | United Kingdom. |
| 2086224 | 5/1982 | United Kingdom. |
| 2095108 | 9/1982 | United Kingdom. |

OTHER PUBLICATIONS

Japanese application 57-58617, together with non-certified English translation.
Patent Abstract of Japan, vol. 9, No. 66 (C-271)[1789]3/26/85.
Chem. Abstract, vol. 98, No. 16 (Apr. 18, 1983).
EPO Laid-Open Application 062682 Nippon Kayaku Kabushiki Kaisha.

Primary Examiner—Delbert R. Phillips
Assistant Examiner—Nathan M. Nutter
Attorney, Agent, or Firm—Donald M. Sell; James A. Smith; Robert W. Sprague

[57] ABSTRACT

A pressure-sensitive adhesive tape for delivering nitroglycerin to skin, the tape comprising a backing with a layer of inert pressure-sensitive adhesive attached thereto, said pressure-sensitive adhesive layer comprising a pressure-sensitive adhesive polymer, skin penetration-enhancing ingredients and a relatively high concentration of nitroglycerin. The tape is useful for systemic treatment of angina pectoris, control of hypertension and treatment of congestive heart failure.

30 Claims, 1 Drawing Sheet

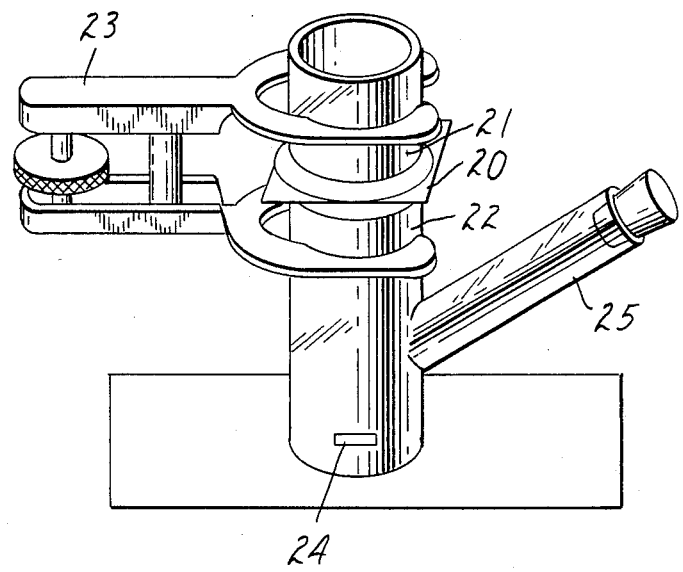

TRANSDERMAL NITROGLYCERIN DELIVERY SYSTEM

BACKGROUND OF THE INVENTION

This invention relates to a pressure-sensitive tape containing nitroglycerin (NTG) in the adhesive portion of the tape, and to a method of treating angina and/or controlling hypertension and/or treating congestive heart failure.

Nitroglycerin is a known drug sold for the treatment of angina, particularly prophylactic treatment of angina.

Numerous formulations which provide nitroglycerin for delivery to and through the skin are known. In general these formulations require complex reservoir and sustained release systems. Many require several different layers.

Inclusion of nitroglycerin in solution in the adhesive portion of a pressure-sensitive adhesive tape is known. One such tape system is that described in EPO laid open application No. 062682. This application discloses adhesive copolymers of dodecyl methacrylate with one or more monomers such as acrylamide or acrylic acid. The EPO application states that adhesive copolymers of alkyl acrylates or alkyl methacrylates in which the alkyl group contains 4–12 carbon atoms have a high ability to absorb nitroglycerin and therefore do not release sufficient amounts of nitroglycerin to skin. Hence, the invention set forth in the EPO application relates to the apparent finding that adhesives prepared from dodecyl methacrylate provide formulations with improved release of nitroglycerin from the adhesive layer. The adhesive layer of the prior art tape additionally may contain what are termed "softeners", which are said to improve adhesion to skin and control the retention and release of nitroglycerin. Examples of such softeners are long chain fatty acid esters such as isopropyl myristate, and fatty acid monoglycerides such a glycerol monostearate. Nitroglycerin is included in the adhesive in the amount of 1–20 mg per 100 cm$^2$ of the tape. Several of the Examples of this application specify adhesive formulations which contain nitroglycerin in an amount of 2% by weight based on the weight of the adhesive copolymer.

U.S. Pat. No. 3,742,951 discloses a nitroglycerin transdermal tape which comprises nitroglycerin contained in a discrete reservoir layer or microcapsules. A transporting aid such as aliphatic esters is also disclosed as being useful.

U.S. Pat. No. 4,485,087 discloses a transdermal tape which comprises a backing and an adhesive layer which may contain a variety of medicaments including nitroglycerin. The backing is one which allows the medicament to migrate therethrough so as to function as a reservoir for the medicament. In making the transdermal tape, the medicament is added to the adhesive in a concentration higher than the solubility of the medicament in the adhesive, and excess medicament is said to migrate into the backing. A variety of adhesives are disclosed including acrylic adhesives.

The use of glyceryl monolaurate as a penetration enhancer for transdermal administration of medicaments has been suggested previously.

Isopropyl myristate is a known penetration enhancer for transdermal administration of medicaments.

BRIEF SUMMARY OF THE INVENTION

The present invention provides a novel adhesive-coated sheet material comprising:
(a) a flexible backing; and
(b) a pressure-sensitive adhesive-coating comprising a homogeneous mixture of:
(i) an acrylic adhesive polymer comprising, as a major constituent, a hydrophobic monomeric acrylic or methacrylic acid ester of an alkyl alcohol, the alkyl alcohol containing about 4 to 10 carbon atoms; and
(ii) nitroglycerin in an amount by weight of about 20 to 45 percent of the total weight of the adhesive coating;
the adhesive-coated sheet material being suitable for substantially continuous transdermal delivery of nitroglycerin to a subject over a prolonged period in an amount which is therapeutically effective for prophylactically treating angina pectoris and/or controlling hypertension and/or treating congestive heart failure.

The present invention also provides a preferred, novel adhesive-coated sheet material comprising:
(a) a flexible backing; and
(b) a pressure-sensitive adhesive-coating comprising a homogeneous mixture of:
(i) a pressure-sensitive acrylic adhesive copolymer comprising A and B monomers as follows:
A is a hydrophobic monomeric acrylic or methacrylic acid ester of an alkyl alcohol, the alkyl alcohol containing 4 to 10 carbon atoms, the A monomer being present in an amount by weight of about 80 to 98 percent of the total weight of all monomers in the copolymer; and
B is a reinforcing monomer selected from the group consisting of acrylic acid, methacrylic acid, an alkyl acrylate or methacrylate containing one to 3 carbon atoms in the alkyl group, acrylamide, methacrylamide, tertiary-butyl acrylamide, diacetone acrylamide, a vinyl ether, a substituted ethylene and a vinyl ester, the B monomer being present in an amount by weight of about 2 to 20 percent of the total weight of all monomers in the copolymer; and
(ii) nitroglycerin in an amount by weight of about 20 to 45 percent of the total weight of the adhesive coating;
the adhesive-coated sheet material being suitable for substantially continuous transdermal delivery of nitroglycerin to a subject over a prolonged period in an amount which is therapeutically effective for prophylactically treating angina pectoris and/or controlling hypertension and/or treating congestive heart failure.

The adhesive coating of the tapes of the invention may optionally comprise as a skin penetration enhancing combination (i) a fatty acid ester prepared from a fatty acid containing about 14 to 20 carbon atoms and an alkyl alcohol containing 2 to about 6 carbon atoms and a single hydroxyl, and (ii) glyceryl monolaurate, the fatty acid ester being present in an amount by weight of about 1 to 30 percent of the total weight of the adhesive coating, and glyceryl monolaurate being present in an amount by weight of about 0.2 to 5 percent of the total weight of the adhesive coating. When such a skin penetration enhancing combination is employed, the nitroglycerin content in the adhesive coating may be about 10 to 45 percent by weight of the total weight of the adhesive coating.

BRIEF DESCRIPTION OF THE DRAWING

The invention may be better understood by reference to the accompanying drawing wherein:

The drawing is an isometric view of a diffusion cell for measuring flux of nitroglycerin across mammalian skin.

DETAILED DESCRIPTION OF THE INVENTION

The present invention relates to pressure-sensitive adhesive tapes comprising a backing and a layer of pressure-sensitive adhesive containing nitroglycerin coated thereon. This invention also relates to an adhesive formulation for preparing such a pressure-sensitive adhesive tape. Further, this invention also relates to a method of treating angina.

By "treating angina" is meant administering a dose of nitroglycerin in an amount at a rate which eliminates or reduces angina pectoris. By "controlling hypertension" is meant administering a dose of nitroglycerin in an amount at a rate which reduces blood pressure. By "treating congestive heart failure" is meant administering a dose of nitroglycerin in an amount which will increase the venous capacitance thus decreasing the left ventricular filling pressure in the heart.

The adhesives utilized in the practice of the invention should be substantially chemically inert to nitroglycerin. Suitable acrylic adhesive polymers comprise, as a major constituent (i.e., at least about 80% by weight of all monomers in the polymer), a hydrophobic monomeric acrylic or methacrylic acid ester of an alkyl alcohol, the alkyl alcohol containing about 4 to 10 carbon atoms. Examples of suitable monomers are those discussed below in connection with the "A Monomer". These adhesive polymers may further comprise minor amounts of other monomers such as the "B monomers" listed below.

Preferred adhesives are acrylic pressure-sensitive adhesive copolymers comprising A and B monomers as follows: Monomer A is a hydrophobic monomeric acrylic or methacrylic acid ester of an alkyl alcohol, the alkyl alcohol containing 4 to 10 carbon atoms, preferably 6 to 10 carbon atoms, more preferably 6–8 carbon atoms, and most preferably 8 carbon atoms. Examples of suitable A monomers are n-butyl, n-pentyl, n-hexyl, isoheptyl, n-nonyl, n-decyl, isohexyl, 2-ethyloctyl, isooctyl and 2-ethylhexyl acrylates. The most preferred A monomer is isooctyl acrylate.

Monomer B is a reinforcing monomer selected from the group consisting of acrylic acid; methacrylic acid; alkyl acrylates and methacrylates containing one to 3 carbon atoms in the alkyl group; acrylamide; methacrylamide; lower alkyl-substituted acrylamides (i.e. the alkyl group containing one to about 4 carbon atoms) such as tertiary-butyl acrylamide; diacetone acrylamide; N-vinyl-2-pyrrolidone; vinyl ethers such as N-tertiary-butyl ether; substituted ethylenes such as derivatives of maleic, fumaric, itaconic, and citraconic acid including maleic anhydride, dimethyl itaconate and monoethyl fumarate; and vinyl esters such as vinyl acetate, vinyl formate and vinyl perfluoro-n-butyrate. The preferred B monomers are acrylic acid, methacrylic acid, the above-described alkyl acrylates and methacrylates, acrylamide, methacrylamide, and the above-described lower alkyl substituted acrylamides. The most preferred B monomer is acrylamide.

The pressure-sensitive adhesive copolymer which comprises A and B monomers as set forth above comprises the A monomer in an amount by weight of about 80 to 98% of the total weight of all monomers in the copolymer. The A monomer is preferably present in an amount by weight of about 88 to 96%, and is most preferably present in an amount by weight of 90 to 94%.

The B monomer in such a copolymer is present in the pressure-sensitive adhesive copolymer in an amount by weight of about 2 to 20 percent, preferably about 6 to 12 percent, and more preferably 6 to 10 percent of the total weight of the monomers in the copolymer.

Of course, the adhesive polymer may contain trace amounts of other conventional non-essential monomers so long as the monomer itself or the amount thereof employed does not significantly adversely affect skin adhesion or the stability or release of nitroglycerin, or result in irritation of skin of mammals.

The adhesive copolymers of the above type are known and their method of preparation is well known to those skilled in the art, having been described, for example, in U.S. Pat. No. RE. 24,906 of Ulrich, incorporated herein by reference. Since the pressure-sensitive adhesives described above are inherently rubbery and tacky and are suitably heat and light stable, there is no need to add tackifiers or stabilizers. However, such may be added if desired.

The nitroglycerin is present in the adhesive in a pharmaceutically effective amount. Generally this amount will be from about 10 to 45% by weight of the total weight of the pressure-sensitive adhesive layer of the tape, and will preferably be about 20 to 35% by weight of the total weight of the adhesive layer. Most preferred is an amount of about 25 to 30% by weight. When the penetration enhancers are not included, the amount of NTG present should be about 20% to 45% by weight, and preferably about 25% to 35%.

The backing of the tape may be occlusive, non-occlusive or a breathable film. The backing may be any of the normal backing materials for pressure-sensitive adhesive tapes such as polyethylene, particularly low-density polyethylene, linear low density polyethylene, high density polyethylene, randomly-oriented nylon fibers, polypropylene, ethylene-vinyl acetate copolymer, polyurethane, rayon and the like. The backing can be optionally microporous or macroporous, examples of such being those described in U.S. Pat. Nos. 3,121,021 and 3,214,501, incorporated herein by reference. The backing should be substantially non-reactive with nitroglycerin.

The backing will play a significant role in the rate of penetration of the nitroglycerin through the skin. Using an occlusive backing such as polyethylene will significantly enhance penetration when compared to a relatively non-occlusive backing such as a rayon nonwoven web or a breathable film such as polyurethane. This variability in rate of penetration allows convenient tailoring of the properties of the formulation while using a relatively limited group of adhesives.

The presently preferred backing is low density polyethylene.

The preferred low density polyethylene backings of the invention are surprisingly good for use in the tapes of the invention. They provide an excellent barrier to loss of NTG when used in combination with the adhesive-NTG formulations of the invention, including those formulations which contain combinations of glyceryl monolaurate and a fatty acid ester. These backings also permit only a minimal uptake of nitroglycerin into the backing.

Backings which were layered such as polyethylene-aluminum-polyethylene composites are also suitable. The aluminum layer may also be a coating such as a vapor coating which serves to reduce migration of nitroglycerin.

It has been found that butyl stearate, ethyl oleate and their equivalents such as other fatty acid esters prepared from a fatty acid containing about 14 to 20 carbon atoms and an alkyl alcohol containing 2 to about 6 carbon atoms and a single hydroxy act as penetration enhancers in the formulations of the invention. Relatively high amounts of, e.g., n-butyl stearate or ethyl oleate, particularly when used in combination with glyceryl monolaurate, significantly enhance the penetration of nitroglycerin in vitro when this phenomena is measured using the hairless (nude mouse skin may be used as an alternative) mouse skin model as described hereinbelow. The preferred adhesive tape of the invention has an adhesive coating comprising a fatty acid ester in an amount of about 2 to 30% by weight, and preferably about 2 to 15% by weight.

It has been found that fatty acid monoglycerides such as glyceryl monolaurate, when added to the adhesive, accentuate the penetration enhancement effect of a fatty acid ester such as ethyl oleate or n-butyl stearate which may be used as components of the formulations. Glyceryl monolaurate itself, without such a fatty acid ester present, shows little enhancement of the penetration of nitroglycerin (NTG) through the skin, this being possibly attributable in part to the fact that glyceryl monolaurate exhibits relatively poor solubility in the adhesive polymer itself. When glyceryl monolaurate and a fatty acid ester (in the amounts described above) are added to and combined in the adhesive of tapes of the invention, a large penetration enhancement is observed It is preferred to use 0.2 to 5% by weight of glyceryl monolaurate based on the total weight of the adhesive coating, and most preferred is about 0.5 to 2% by weight. It is also preferred to have a ratio of 6 parts by weight of the fatty acid ester to 1 part by weight of the glyceryl monolaurate.

The preferred fatty acid ester for use with glyceryl monolaurate is ethyl oleate. A preferred glyceryl monolaurate is that commercially available from Lauricidin, Inc. (Monroe, Mich.) under the trade designation lauricidin (distilled monoglyceride).

Although animal skins are known to give significant quantitative differences in drug penetration rates versus human skin, a rank order correlation is generally observed with various drugs (M. J. Bartek and J. A. La-Budde in "Animal Modes in Dermatology", H. Maibach, Ed., Churchill Livingstone, N.Y., 1975, pp. 103–119). Hairless mouse skin has been recommended as a readily available animal skin for use in diffusion cells with steroids and small molecules (R. B. Stoughton, Arch. Derm., 99, 753 (1969), J. L. Cohen and R. B. Stoughton, J. Invest. Derm., 62, 507 (1974), R. B. Stoughton, in "Animal Modes in Dermatology", H. Maibach, Ed., Churchill Livingston, N.Y., 1975, pp. 121–131).

In the specific test procedure used herein, hairless mouse skin removed from female hairless mice (available from Jackson Laboratory, Strain HRS/J, age 2–5 months) is used. It is maintained on ice until about 30 minutes before use. The mouse skin is cut in half and each half is mounted, or the skin is used whole, on a diffusion cell of the type shown in the drawing. The cell is modeled after those described in the litarature (e.g. J. L. Cohen, R. B. Stoughton, J. Invest. Dermatol., 62, 507 (1974) and R. B. Stoughton, Arch. Derm., 99, 753 (1964). As shown in the FIGURE, the mouse or human skin 20 is mounted epidermal side up between the upper and lower portions of the cell 21 and 22, which are held together by means of a ball joint clamp 23. The cell below the skin is filled with 0.01M phosphate buffer, pH about 6.9 to 7, with ionic strength adjusted to 0.155 with sodium chloride to act as the "acceptor" fluid. Sodium azide in concentrations of about 0.2 g/l is added to prevent biological degradation of NTG in the acceptor solution. The acceptor fluid is stirred using a magnetic stirring bar 24 and a magnetic stirrer (not illustrated). The sampling port 25 is stoppered except when in use.

A known amount of a formulation to be evaluated is applied to the epidermal (upper) side of the skin in a uniform layer as follows: The desired amount of formulation or area of a tape formulation is accurately determined so that the amount of adhesive applied to the cell can be accurately determined. The formulation is applied to the skin already mounted in the diffusion cell and spread about to give a uniform layer or in the case of a tape pressed to cause uniform contact to the skin.

The cell is then placed in a constant temperature (34° to 35° C.) constant humidity chamber (generally maintained at a humidity between 50 and 70%, preferably about 60%) and kept there throughout the experiment. The chamber utilizes a heat exchanger coupled to a constant temperature bath, with a fan to circulate air. A saturated calcium nitrate solution is used to maintain the humidity. The acceptor fluid is stirred by means of a magnetic stirring bar throughout the experiment to assure a uniform sample and a reduced diffusion layer on the dermal side of the skin. The acceptor fluid is removed at specified time intervals and fresh buffer is added to replace the withdrawn fluid immediately. The withdrawn aliquots are analyzed for drug content by conventional high pressure liquid chromatography and the cumulative amount of the drug penetrating the skin is calculated. Plots of the cumulative drug penetration as a function of time give a profile of drug flux measured in $\mu g/cm^2/hour$.

The use of other skin such as pig skin and human skin in the above apparatus has confirmed the utility of the formulations of the invention.

Further testing has demonstrated, by the presence of nitroglycerin in the blood of pigs, that nitroglycerin is absorbed through pig skin in significant levels from formulations of the invention. Steady state levels are attained readily and are maintained for many hours.

The tapes of the present invention are preferably prepared by the addition of a solution of nitroglycerin in ethanol or ethyl acetate to an organic solution containing the adhesive copolymer. Preferred organic solvents for preparing the adhesive solution are methanol and ethyl acetate. The nitroglycerin solution is prepared by methods known to the art, e.g., by extracting nitroglycerin from an NTG/lactose triturate into a solvent which is compatible with the adhesive such as ethyl acetate (preferably) or ethanol. After mixing the adhesive solution with the nitroglycerin solution, the penetration enhancer(s) are added to and mixed into the formulation to prepare a final coating solution with a total solid content in the range of 15 to 40% (preferably 20 to 30%). The formulation may be wet cast or coated by wet-cast or knife coating techniques to provide a predetermined uniform thickness of the wet adhesive formulation onto a suitable release liner. This sheet is then dried and laminated onto a backing material using conventional methods. It is preferred to corona-treat the surface of the polyethylene backing intended for contact with the adhesive. Suitable release liners are known silicone-type release liners such as that available under the trade designation Daubert 164Z, from Daubert Co. which are coated onto polyester film.

The adhesive-coated sheet material of the invention may be in the form of a tape, a patch, a sheet, a dressing or other forms known to the art as will be apparent to one skilled in the art. Preferably, the adhesive coated sheet material will contain about 5 to 25 mg, and preferably about 10 to 18 mg, of nitroglycerin per 5 $cm^2$ of the sheet material. Further, the sheet material will generally be about 1 to 30 $cm^2$, and preferably about 1 to 10 $cm^2$, in dimension.

Generally, a transdermal patch of the invention will be applied to the upper torso of a mammal (preferably a human) and will be replaced with a fresh patch as required to maintain the therapeutic effect. Those skilled in the art may easily determine the frequency at which the patches of the invention should be replaced to achieve the desired therapeutic effect.

The following examples are provided to illustrate the invention. Parts and percentages are by weight unless otherwise specified. Flux rates are expressed in units of micrograms of NTG per $cm^2$ (of skin) per hour (hereinafter $\mu g/cm^2/hour$) and cumulative penetration is expressed in units of the percent of the total amount of NTG contained in adhesive which passes through the skin during a particular time period. Each result represents the average value of several (e.g., 3 to 5) independent determinations.

Inherent Viscosity Measurement

In the Examples which follow, it is useful to refer to the molecular weight of the adhesive polymer used in the adhesive formulations. The comparative molecular weights are determined by measuring the viscosity of dilute solutions of the adhesives prepared according to these teachings.

The inherent viscosity values which are reported in the Examples which follow were obtained by the conventional method used by those skilled in the art. The measurement of the viscosity of dilute solutions of the adhesive, when compared to controls run under the same conditions, clearly demonstrate the relative molecular weights. It is the comparative values which are significant and absolute figures are not required. In the examples, the inherent viscosity values were obtained using a Cannon-Fenske #50 viscometer in a water bath controlled at 25° C. to measure the flow time of 10 ml of a polymer solution (0.2 g per deciliter polymer in tetrahydrofuran). The examples and controls being run for comparison were run under identical conditions. The test procedure followed and the apparatus used are explained in detail in the Textbook of Polymer Science, F. W. Billmeyer, Wiley-Interscience, 2nd Edition, 1971 under: Polymer chains and their characterization, D. Solution viscosity and Molecular Size, pages 84 and 85.

EXAMPLE 1

General Procedure for Preparing Nitroglycerin Formulations.

Part A

Preparation of Nitroglycerin Solution

Nitroglycerin is commercially available as a triturate of 10% NTG on lactose. A NTG solution is obtained by diluting the triturate with an equal weight of ethyl acetate and mixing thoroughly. After about one hour of soaking with occasional stirring the NTG solution is separated by filtration using sintered glass, which does not absorb NTG, to provide a solution of 15 to 25% NTG.

Part B

Preparation of Nitroglycerin-Adhesive Mixture

To a 40% solids solution of an adhesive copolymer in ethyl acetate was added an approximately equal weight of the solution of NTG from Part A. The mixture was mixed in a glass container for about 16 hours to obtain thorough mixing.

Part C

Preparation of a Nitroglycerin-Adhesive-Enhancer Formulation

To the NTG-adhesive mixture from Part B was added as a penetration enhancing combination a solution of ethyl oleate and glyceryl monolaurate. The mixture of ethyl oleate and glyceryl monolaurate was prepared by warming while mixing the two components until even distribution and a clear solution of the components was obtained.

If it is desired to increase the concentration of NTG, additional solution from Part A may be added at this time. After mixing the NTG-adhesive mixture with the enhancer the bubbles were allowed to dissipate by standing in a sealed system to prevent solvent loss prior to coating.

Part D

Preparation of a Coated NTG Formulation

A knife-coater was used to coat the formulation from Part C. onto a layer of perfluoropolyether release liner at a thickness of about 0.022 inches. The formulation was then laminated onto a backing of extruded polyethylene-aluminum-polyethylene composite, Scotchpak ® 1006 (3M, St. Paul, Minn.).

This formulation was punched, die-cut or otherwise cut to provide patches for application to skin or for testing for NTG delivery using in vitro or in vivo models.

EXAMPLE 2

A pressure-sensitive adhesive copolymer comprising isooctyl acrylate and acrylamide (96:4) was prepared as follows:

Acrylamide, 3.2 g, 76.8 g of isooctyl acrylate, 0.12 g of benzoyl peroxide and 120 g of ethyl acetate were added to a brown quart bottle and mixed. The above procedure was then repeated to provide a second batch. The bottles were purged with nitrogen for 4 minutes (at a rate of one liter per minute), sealed and placed in a launderometer at 55° C. for 24 hours. The resulting polymer lots had an inherent viscosity of 1.62 and 1.66.

Using the general method described in Example 1, the formulations shown in Table I were prepared using the adhesive copolymer solution obtained above. Penetration through pig skin was measured using 4 samples of skin per formulation using the diffusion apparatus and method described in the specification, and averaging the results.

TABLE I

| Formulation | Cumulative % Penetration | |
| --- | --- | --- |
| | 11 Hours | 24 Hours |
| 34.5% NTG<br>1.4% glyceryl monolaurate<br>8.2% ethyl oleate<br>55.9% adhesive | 2.7 | 6.4 |
| 33.5% NTG<br>12.0% ethyl oleate<br>5.0% butyl stearate<br>49.5% adhesive | 1.5 | 4.1 |
| 34.0% NTG<br>8.2% isopropyl myristate<br>57.8% adhesive | 1.1 | 2.8 |

EXAMPLE 3

Using the general method of Example 1, four formulations described in Table II below were prepared, again using the adhesive copolymer solution prepared in Example 2. The penetration of NTG through human skin (5 samples per formulation) was measured for each of the formulations using the diffusion cell and method previously described. The adhesive used was the copolymer of isooctyl acrylate:acrylamide (96:4), and patches which measured 2.06 cm$^2$ were employed. The flux rates and cumulative percent penetration ("C%P") observed were as indicated in Table II.

TABLE II

| Formulation | 5 hours | | 12 hours | | 24 hours | |
| --- | --- | --- | --- | --- | --- | --- |
| | Flux | C % P | Flux | C % P | Flux | C % P |
| (A)<br>28% NTG<br>2% glyceryl monolaurate<br>12% ethyl oleate<br>58% adhesive | 35.7 | 5.9 | 39.9 | 15.9 | 38.9 | 31.1 |
| (B)<br>27.9% NTG<br>12.3% ethyl oleate<br>59.8% adhesive | 27.0 | 4.5 | 31.1 | 12.5 | 30.9 | 24.9 |
| (C)<br>28% NTG<br>2.1% glyceryl monolaurate<br>69.9% adhesive | 29.0 | 4.9 | 29.7 | 12.0 | 30.2 | 24.4 |
| (D)<br>28% NTG<br>72% adhesive | 25.4 | 4.4 | 26.5 | 11.0 | 25.7 | 21.4 |

This experiment demonstrates higher total penetration and flux rate in the presence of both ethyl oleate and glyceryl monolaurate (Formulation A) as compared to Formulations B and C which contained only one of ethyl oleate and glyceryl monolaurate, respectively.

EXAMPLE 4

In an in vivo study the delivery of NTG to the bloodstream of pigs was determined using an adhesive tape of the invention in which the adhesive layer comprised a copolymer of isooctyl acrylate:acrylamide (93:7), 30% nitroglycerin, 2% glyceryl monolaurate and 12% ethyl oleate. The adhesive copolymer was prepared generally as described in Example 6. In preparing the adhesive tape using the above adhesive copolymer, the procedures of Example 1 were followed. The patch was 19.5 cm$^2$ and was placed behind the ear. Patches were changed every 24 hours. By analysis of plasma, it was found that the flux rate exhibited by the adhesive tape of this Example provided 2 to 8 nanograms of NTG per milliliter of serum after 12 hours.

EXAMPLE 5

Preparation of Adhesive Copolymer

A pressure-sensitive adhesive copolymer comprising isooctyl acrylate and acrylamide (92:8) was prepared as follows:

Acrylamide, 81.9 g, and 2.05 g of benzoyl peroxide were dissolved in a mixture of 1382.4 g of ethyl acetate and 153.6 g of methanol. Isooctyl acrylate, 942.1 g, was then added to the resulting solution which was then mixed. Five 500 g portions of the above were each placed in 1-quart amber bottles which were then purged with nitrogen at the rate of one liter per minute for two minutes. The procedure was repeated to provide a second batch of polymer. The bottles were sealed and placed in a launderometer operated at 55° C. for 24 hours. Samples of polymer taken from one of the quart bottles from each lot were determined to have inherent viscosities of 0.98 and 1.01.

Preparation of Transdermal Patch

Part A

A 25-30 percent solids solution of the isooctyl acrylate:acrylamide (92:8) adhesive copolymer in ethyl acetate/methanol (90:10) was coated onto a 2-sided release liner using a knife-coater and coating at 20 mils in thickness. The adhesive-coated laminate was dried first at 180° F. for 3 minutes and then at 240° F. for 3 minutes. The dried adhesive coating was then stripped off the release liner and placed into a small glass bottle. A sufficient amount of a mixture of ethyl acetate/methanol (90:10) was added to the contents of the bottle to provide a 38% solids solution of the adhesive. The foregoing procedure results in a reduction of the amount of residual monomer which may be contained in the adhesive copolymer.

Part B

A triturate of 10% nitroglycerin on lactose (commercially available under the trade designation from ICI Americas, Inc.) was mixed with an equal weight of ethyl acetate. After about one hour of soaking with occasional stirring, the nitroglycerin solution is separated by filtration using a sintered glass filter to provide a solution of nitroglycerin containing 16.2% nitroglycerin.

Part C

Six parts of ethyl acetate and one part of glyceryl monolaurate were mixed with warming until a clear solution was obtained.

Part D

To 185.03 g of the 38% solids adhesive solution obtained in Step A was added 240.71 g of the nitroglycerin solution obtained in Step B, and 10.8 g of the ethyl oleate-glyceryl monolaurate mixture obtained in Part C. The mixture was mixed in a glass container for about 16 hours to achieve thorough mixing. After thorough mixing, the bubbles were allowed to dissipate in the container which was sealed to prevent solvent loss.

Part E

The mixture obtained in Part D was coated onto a 5-mil Daubert 164Z polyester release liner using a knife coater to provide a coating which was about 20 mils in thickness. The laminate was dried first at 125° F. for 4 minutes and then at 210° F. for 2 minutes. After being allowed to stand for about one hour, the dried adhesive formulation was then laminated onto a 3-mil low density polyethylene backing which had been corona treated. The resulting backing-adhesive-release liner laminate was then die-cut to provide 5.07 cm² patches which were determined to contain 14.33 mg of nitroglycerin per patch (30.96% nitroglycerin based on the weight of the adhesive coating).

Part F

The release liner was removed from the patches obtained in Part E and the patches were then applied to female hairless mouse skin. Using the cell described previously and operated as described previously, the following flux rates and cumulative % penetration ("C%P") were observed at the indicated time intervals:

| 4 Hours | | 8 Hours | | 12 Hours | | 24 Hours | |
|---|---|---|---|---|---|---|---|
| Flux | C % P | Flux | C % P | Flux | C % P | Flux | C % P |
| 31.4 | 5.1% | 47.0 | 15.4% | 52.7 | 25.9% | 45 | 44.1% |

EXAMPLE 6

Preparation of Adhesive Copolymer

A pressure-sensitive adhesive copolymer comprising isooctyl acrylate and acrylamide (93:7) was prepared in accordance with the procedures of Example 5 using the following ingredients: 952.3 g of isooctyl acrylate; 71.7 g of acrylamide; 2.05 g of benzoyl peroxide; 1382.4 g of ethyl acetate; and 153.6 g of methanol. A second batch of polymer was also prepared. Samples of polymer taken from one of the quart bottles from each lot were determined to have an inherent viscosities of 1.29 and 1.30.

Preparation of Transdermal Patch

Part A

A 25-30 percent solids solution of the isooctyl acrylate:acrylamide (93:7) adhesive copolymer in ethyl acetate/methanol (90:10) was coated onto a release liner, dried and redissolved in ethyl acetate/methanol (90:10) as described in Example 5, Part A, to provide a 38.7% solids solution of the adhesive.

Alternatively, to reduce residual monomer to even lower levels, a 5% solids solution of the adhesive copolymer may instead be coated onto a release liner in a thickness of 5 mils, followed by drying at 250° F. for 30 minutes. The dried adhesive may then be redissolved in ethyl acetate methanol (90:10) as described previously. This alternative procedure, however, was not used in this or subsequent Examples.

Part B

To 195.99 g of the adhesive solution obtained in Part A of this Example was added 242.69 g of a nitroglycerin solution prepared as described in Example 5, Part B (except that here the nitroglycerin solution contained 16% nitroglycerin), and 8.41 g of the ethyl oleate/glyceryl monolaurate solution obtained in Example 5, Part C. The mixture was mixed in a glass container for about 16 hours, and the bubbles were then allowed to dissipate as discussed in Example 5, Part D.

Part C

Patches comprising the adhesive mixture prepared in part B of this Example were then prepared in accordance with the procedures of Example 5, Part E, except that here 2.06 cm² patches were prepared. The nitroglycerin content was determined to be 31.25% based on the weight of the adhesive coating.

Part D

Cumulative % penetration ("C%P") was then determined for the patches obtained in Part C of this Example in accordance with the procedures of Example 5, Part F, except that human skin was used. Results observed at the indicated time intervals were as follows:

| 3 Hours C % P | 6 Hours C % P | 10 Hours C % P | 24 Hours C % P |
|---|---|---|---|
| 4.9% | 11.4% | 19.3% | 43.2% |

EXAMPLE 7

Part A

A 25-30 percent solids solution of isooctyl acrylate:acrylamide (92:8) adhesive copolymer in ethyl acetate:methanol (90:10) (prepared as described in Example 5) was coated at 20-mils thickness onto a 2-sided release liner and dried first at 180° F. for 3 minutes and then at 240° F. for 3 minutes. The coated adhesive laminate was then wound up on itself for convenience. The adhesive coating was removed from the release liner. Treatment of the adhesive in the foregoing manner results in a reduction of residual monomer which may be present in the adhesive.

Part B

The following were added to a small glass bottle: 76.61 g of the adhesive copolymer obtained in Part A of this Example; 200.00 g of a nitroglycerin solution prepared as described in Example 5, Part B, except that here the solution contained 16.2% nitroglycerin; 10.82 g of the ethyl oleate-glyceryl monolaurate solution prepared in Example 9, Part C; and 125.99 g of ethyl acetate:methanol (90:10). The glass bottle was sealed and shaken to produce a homogeneous mixture.

Part C

The mixture obtained in Part B of this Example was coated in a thickness of 20-mils onto a 5-mil Daubert 164Z polyester release liner, and dried first at 125° F. for 4 minutes and then at 210° F. for 2 minutes. After being allowed to stand for about one hour, the laminate was then laminated onto a 3-mil low density polyethylene backing which had been corona treated. The resulting backing-adhesive-release liner laminate was die-cut to provide 5.07 cm² patches which were determined to contain 25.56% nitroglycerin based on the weight of the adhesive coating.

Part D

When a patch prepared above was tested in accordance with the procedure of Example 5, Part G, the following flux rates were observed at the indicated time intervals:

| 4 Hours | 8 Hours | 12 Hours | 24 Hours |
| --- | --- | --- | --- |
| 28.4 | 45.8 | 48.1 | 45.6 |

EXAMPLE 8

Part A

A 25–30 percent solids solution of isooctyl acrylate:acrylamide (93:7) adhesive copolymer in ethyl acetate:-methanol (90:10) (prepared as described in Example 6) was treated in accordance with the procedures of Example 7, Part A.

Part B

The following were mixed in accordance with the procedures of Example 7, Part B: 79.47 g of the adhesive copolymer obtained in Part A of this Example; 200.00 g of a nitroglycerin solution prepared as described in Example 5, Part B; 8.41 g of the ethyl oleate-glyceryl monolaurate solution prepared in Example 5, Part C; and 130.26 g of ethyl acetate:methanol (90:10).

Part C

Patches were prepared using the mixture obtained in Part B of this Example in accordance with the procedures of Example 7, Part C. The nitroglycerin content was determined to be 25.55% based on the weight of the adhesive coating.

Part D

When a patch prepared above was tested in accordance with the procedures of Example 5, Part G, the following flux rates were observed at the indicated time intervals:

| 4 Hours | 8 Hours | 12 Hours | 24 Hours |
| --- | --- | --- | --- |
| 28.4 | 48.2 | 51.1 | 50.9 |

EXAMPLE 9

A 15% solids solution of polybutyl acrylate having an inherent viscosity of 2.0–2.8 was coated onto a release liner using a knife coater and in a thickness of about 20 mils. The laminate was allowed to air-dry overnight, and the dried adhesive was then removed from the laminate. An adhesive formulation was then prepared using the following ingredients: 7.67 g of the dried adhesive polymer, 15.63 g of a nitroglycerin solution containing 15.9% nitroglycerin in ethyl acetate; and 26.10 g of an ethyl acetate:methanol blend (90:10). The above mixture was coated onto a release liner at a thickness of 20 mils using a knife coater. The laminate was then dried, laminated to a backing and die-cut, all as described in Example 7 Part C to provide 5.07 cm² patches which were determined to contain 24.4% nitroglycerin based on the weight of the adhesive coating.

When tested using mouse skin and the diffusion cell and method described previously, the following flux rates and cumulative % penetration ("C%P") were observed at the indicated time intervals:

| 10 Hours | | 17 Hours | |
| --- | --- | --- | --- |
| Flux | C % P | Flux | C % P |
| 4.73 | 3.2% | 5.40 | 6.3% |

I claim:
1. An adhesive-coated sheet material comprising:
   (a) a flexible backing; and
   (b) a pressure-sensitive adhesive-coating comprising a homogeneous mixture of:
      (i) an acrylic polymer comprising, as a major constituent, a hydrophobic monomeric acrylic or methacrylic acid ester of an alkyl alcohol, the alkyl alcohol containing 4 to 10 carbon atoms; and
      (ii) nitroglycerin in an amount by weight of about 25 to 45 percent of the total weight of said adhesive coating;
   said sheet material being suitable for substantially continuous transdermal delivery of nitroglycerin to a subject over a prolonged period in an amount which is therapeutically effective for prophylactically treating angina pectoris and/or controlling hypertension and/or treating congestive heart failure.

2. A method of treating angina and/or controlling hypertension and/or treating congestive heart failure wherein an adhesive-coated sheet material according to claim 1 is applied and adhered to the skin of a mammal.

3. A process for preparing the adhesive-coated sheet material of claim 1, comprising the steps of:
   (a) forming a homogeneous mixture comprising nitroglycerin and said acrylic polymer, said nitroglycerin being present in said mixture in an amount sufficient so that said pressure-sensitive adhesive coating of said adhesive-coated sheet material comprises nitroglycerin in an amount by weight of about 25 to 45 percent of the total weight of said pressure-sensitive adhesive coating;
   (b) wet-casting or coating the homogeneous mixture obtained in step (a) onto a release liner;
   (c) drying the wet-cast or coated homogeneous mixture provided in step (b); and
   (d) lamaminating the dried homogeneous mixture obtained in step (c) to said flexible backing.

4. An adhesive-coated sheet material comprising:
   (a) a flexible backing;
   (b) a pressure-sensitive adhesive-coating comprising a homogeneous mixture of:
      (i) an acrylic polymer comprising, as a major constituent, a hydrophobic monomeric acrylic or methacrylic acid ester of an alkyl alcohol, the alkyl alcohol containing 4 to 10 carbon atoms;
      (ii) a skin penetration enhancing combination comprising (1) ethyl oleate present in an amount by weight of about 2 to 15 percent of the total weight of said adhesive coating; and (2) glyceryl monolaurate which is present in an amount by weight of about 0.2 to 5 percent of the total weight of said adhesive coating, the relative amounts of ethyl oleate and glyceryl monolaurate further being such that said glyceryl monolaurate accentuates the penetration enhancement effect of said ethyl oleate; and
(iii) nitroglycerin in an amount by weight of about 10 to 45 percent of the total weight of said adhesive coating;
said sheet material being suitable for substantially continuous transdermal delivery of nitroglycerin to a subject over a prolonged period in an amount which is therapeutically effective for prophylactically treating angina pectoris and/or controlling hypertension and/or treating congestive heart failure.

5. A method of treating angina and/or controlling hypertension and/or treating congestive heart failure wherein an adhesive-coated sheet material according to claim 4 is applied and adhered to the skin of a mammal.

6. An adhesive-coated sheet material comprising:
(a) a flexible backing; and
(b) a pressure-sensitive adhesive-coating comprising a homogeneous mixture of:
  (i) a pressure-sensitive acrylic adhesive copolymer comprising A and B monomers as follows:
    A is a hydrophobic monomeric acrylic or methacrylic acid ester of an alkyl alcohol, the alkyl alcohol containing 4 to 10 carbon atoms, said A monomer being present in an amount by weight of about 80 to 98 percent of the total weight of all monomers in said copolymer; and
    B is a reinforcing monomer selected from the group consisting of acrylic acid, methacrylic acid, an alkyl acrylate or methacrylate containing one to 3 carbon atoms in the alkyl group, acrylamide, methacrylamide, a lower alkyl-substituted acrylamide, diacetone acrylamide, N-vinyl-2-pyrrolidone, a vinyl ether, a substituted ethylene and a vinyl ester, the B monomer being present in an amount by weight of about 2 to 20 percent of the total weight of all monomers in said copolymer; and
  (ii) nitroglycerin in an amount by weight of about 25 to 45 percent of the total weight of said adhesive coating;
said sheet material being suitable for substantially continuous transdermal delivery of nitroglycerin to an subject over a prolonged period in an amount which is therapeutically effective for prophylactically treating angina pectoris and/or controlling hypertension and/or treating congestive heart failure.

7. An adhesive-coated sheet material according to claim 6, wherein said adhesive copolymer comprises about 2 to 10% by weight of acrylamide and about 90 to 98% by weight of alkyl acrylate wherein the alkyl group contains six to ten carbon atoms.

8. A method of treating angina and/or controlling hypertension and/or treating congestive heart failure wherein an adhesive-coated sheet material according to claim 6 is applied and adhered to the skin of a mammal.

9. A process for preparing the adhesive-coated sheet material of claim 6, comprising the steps of:
(a) forming a homogeneous mixture comprising nitroglycerin and said acrylic polymer, said nitroglycerin being present in said mixture in an amount sufficient so that said pressure-sensitive adhesive coating of said adhesive-coated sheet material comprises nitroglycerin in an amount by weight of about 25 to 45 percent of the total weight of said pressure-sensitive adhesive coating;
(b) wet-casting or coating the homogeneous mixture obtained in step (a) onto a release liner;
(c) drying the wet-cast or coated homogeneous mixture provided in step (b); and
(d) laminating the dried homogeneous mixture obtained in step (c) to said flexible backing.

10. A process according to claim 9, wherein said flexible backing is substantially impermeable to nitroglycerin.

11. An adhesive-coated sheet material comprising:
(a) a flexible backing; and
(b) a pressure-sensitive adhesive-coating comprising a homogeneous mixture of:
  (i) a pressure-sensitive acrylic adhesive copolymer comprising A and B monomers as follows:
    A is a hydrophobic monomeric acrylic or methacrylic acid ester of an alkyl alcohol, the alkyl alcohol containing 4 to 10 carbon atoms, said A monomer being present in an amount by weight of about 80 to 98 percent of the total weight of all monomers in said copolymer; and
    B is a reinforcing monomer selected from the group consisting of acrylic acid, methacrylic acid, an alkyl acrylate or methacrylate containing one to 3 carbon atoms in the alkyl group, acrylamide, methacrylamide, a lower alkyl-substituted acrylamide, diacetone acrylamide, N-vinyl-2-pyrrolidone, a vinyl ether, a substituted ethylene and a vinyl ester, said B monomer being present in an amount by weight of about 2 to 20 percent of the total weight of all monomers in said copolymer.
  (ii) a skin penetration enhancing combination comprising (1) ethyl oleate present in an amount by weight of about 2 to 15 percent of the total weight of said adhesive coating; and (2) glyceryl monolaurate which is present in an amount by weight of about 0.2 to 5 percent of the total weight of said adhesive coating, the relative amounts of ethyl oleate and glyceryl monolaurate further being such that said glyceryl monolaurate accentuates the penetration enhancement effect of said ethyl oleate; and
  (iii) nitroglycerin in an amount by weight of about about 10 to 45 percent of the total weight of said adhesive coating;
said sheet material being suitable for substantially continuous transdermal delivery of nitroglycerin to a subject over a prolonged period in an amount which is therapeutically effective for prophylactically treating angina pectoris and/or controlling hypertension and/or treating congestive heart failure.

12. An adhesive-coated sheet material according to claim 11, wherein said glyceryl monolaurate is present in an amount by weight of about 0.5 to 2 percent.

13. A method of treating angina and/or controlling hypertension and/or treating congestive heart failure wherein an adhesive-coated sheet material according to claim 11 is applied and adhered to the skin of a mammal.

14. An adhesive composition comprising, as a homogeneous mixture,
(i) a pressure-sensitive acrylic adhesive copolymer comprising A and B monomers as follows:

A is a hydrophobic monomeric acrylic or methacrylic acid ester of an alkyl alcohol, the alkyl alcohol containing 4 to 10 carbon atoms, said A monomer being present in an amount by weight of about 80 to 98 percent of the total weight of all monomers in said copolymer; and B is a reinforcing monomer selected from the group consisting of acrylic acid, methacrylic acid, an alkyl acrylate or methacrylate containing one to 3 carbon atoms in the alkyl group, acrylamide, methacrylamide, a lower alkyl-substituted acrylamide, diacetone acrylamide, N-vinyl-2-pyrrolidone, a vinyl ether, a substituted ethylene and a vinyl ester, said B monomer being present in an amount by weight of about 2 to 20 percent of the total weight of all monomers in said copolymer; and (ii) nitroglycerin in an amount by weight of about 25 to 45 percent of the total weight of said adhesive copolymer and nitroglycerin;

said adhesive composition being suitable for substantially continuous transdermal delivery of nitroglycerin to a subject over a prolonged period in an amount which is therapeutically effective for prophylactically treating angina pectoris and/or controlling hypertension and/or treating congestive heart failure.

15. An adhesive composition comprising, as a homogeneous mixture, (i) a pressure-sensitive acrylic adhesive copolymer comprising A and B monomers as follows:

A is a hydrophobic monomeric acrylic acid or methacrylic acid ester of an alkyl alcohl, the alkyl alcohol containing 4 to 10 carbon atoms, said A monomer being present in an amount by weight of about 80 to 98 percent of the total weight of all monomers in said copolymer; and B is a reinforcing monomer selected from the group consisting of acrylic acid, methacrylic acid, an alkyl acrylate or methacrylate containing one to 3 carbon atoms in the alkyl group, acrylamide, methacrylamide, a lower alkyl-substituted acrylamide, diacetone acrylamide, N-vinyl-2-pyrrolidone, a vinyl ether, a substituted ethylene and a vinyl ester, said B monomer being present in an amount by weight of about 2 to 20 percent of the total weight of all monomers in said copolymer;

(ii) a skin penetration enhancing combination comprising (1) ethyl oleate; and (2) glyceryl monolaurate; and (iii) nitroglycerin;

said ethyl oleate, said glyceryl monolaurate and nitroglycerin being present in an amount by weight of about 2 to 15 percent, about 0.2 to 5 percent, and about 10 to 45 percent, respectively, based upon the total weight of said acrylic copolymer, said fatty acid ester, glyceryl monolaurate and nitroglycerin, the relative amounts of ethyl oleate and glyceryl monolaurate further being such that said glyceryl monolaurate accentuates the penetration enhancement effect of said ethyl oleate; said adhesive composition being suitable for substantially continuous transdermal delivery of nitroglycerin to a subject over a prolonged period in an amount which is therapeutically effective for prophylactically treating angina and/or controlling hypertension and/or treating congestive heart failure.

16. An adhesive-coated sheet material comprising:
(a) a flexible-backing; and (b) a pressure-sensitive adhesive-coating contiguously adhered to one surface of said flexible backing and comprising a homogeneous mixture comprising:

(i) an acrylic polymer comprising, as a major constituent, a hydrophobic monomeric acrylic or methacrylic acid ester of an alkyl alcohol, the alkyl alcohol containing 4 to 10 carbon atoms; and (iii) nitroglycerin in an amount of weight of about 25 to 45 percent of the total weight of said adhesive coating;

said flexible backing being substantially impermeable to nitroglycerin contained in said adhesive coating and exhibiting substantially no uptake of nitroglycerin from said adhesive-coating and said sheet material being suitable for substantially continuous transdermal delivery of nitroglycerin to a subject over a prolonged period in an amount which is therapeutically effective for prophylactically treating angina pectoris and/or controlling hypertension and/or treating congestive hear failure.

17. An adhesive-coated sheet material according to claim 16, wherein said pressure-sensitive adhesive-coating further comprises a fatty acid ester prepared from (i) a fatty acid containing about 14 to 20 carbon atoms and (ii) an alkyl alcohol containing 2 to about 6 carbon atoms and a single hydroxy, said fatty acid ester being present in an amount by weight of about 2 to 30% of the total weight of said adhesive coating and resulting in an enhanced penetration of nitroglycerin as compared to when no fatty acid ester is present.

18. An adhesive-coated sheet material according to claim 17, wherein said fatty acid ester is ethyl oleate which is present in an amount by weight of about 2 to 15% of the total weight of said adhesive coating, and wherein said pressure-sensitive adhesive-coating further comprises glyceryl monolaurate in an amount by weight of about 0.2 to 5% of the total weight of said adhesive coating, the relative amounts of said ethyl oleate and said glyceryl monolaurate further being such that said glyceryl monolaurate accentuates the penetration enhancement effect of said fatty acid ester.

19. An adhesive-coated sheet material according to claim 16, wherein nitroglycerin is present in an amount by weight of about 25 to 35% of the total weight of said adhesive coating.

20. An adhesive-coated sheet material according to claim 16, wherein said sheet material contains nitroglycerin in said adhesive coating in an amount providing about 5 to 25 mg nitroglycerin per 5 cm$^2$ of said sheet material.

21. An adhesive-coated sheet material according to claim 16, wherein said backing is occlusive.

22. An adhesive-coated sheet material comprising:
(a) a flexible backing; and
(b) a pressure-sensitive adhesive-coating contiguously adhered to one surface of said flexible backing and comprising a homogeneous mixture comprising:
(i) a pressure-sensitive acrylic adhesive copolymer comprising A and B monomers as follows:

A is a hydrophobic monomeric acrylic or methacrylic acid ester of an alkyl alcohol, the alkyl alcohol containing 4 to 10 carbon atoms, said A monomer being present in an amount by weight of about 80 to 98 percent of the total weight of all monomers in said copolymer; and B is a reinforcing monomer selected from the group consisting of acrylic acid, methacrylic acid, an alkyl acrylate or methacrylate containing one to 3 carbon atoms in the alkyl group, acrylamide, methacrylamide, a lower alkyl-substituted acrylamide, diacetone acrylamide, N-vinyl-2-pyrrolidone, a vinyl ether, a substituted ethylene and a vinyl ester, the B monomer being present in an amount by weight of about 2 to 20 to percent of the total weight of all monomers in said copolymer; and (ii) nitroglycerin in an amount by weight of about 25 to 45 percent of the total weight of said adhesive coating;

said flexible backing being substantially impermeable to nitroglycerin contained in said adhesive coating and exhibiting substantially no uptake of nitroglycerin from said adhesive coating, and said sheet material being suitable for substantially continuous transdermal delivery of nitroglycerin to a subject over a prolonged period in an amount which is therapeutically effective for prophylactically treating angina pectoris and/or controlling heart failure.

23. An adhesive-coated sheet material according to claim 22, wherein said pressure-sensitive adhesive-coating further comprises a fatty acid ester prepared from (i) a fatty acid containing about 14 to 20 carbon atoms and (ii) an alkyl alcohl containing 2 to about 6 carbon atoms and a single hydroxy, said fatty acid ester being present in an amount by weight of about 2 to 30% of the total weight of said adhesive coating and resulting in an enhanced penetration of nitroglycerin as compared to when no fatty acid ester is present.

24. An adhesive-coated sheet material according to claim 23, wherein said fatty acid ester is ethyl oleate which is present in an amount by weight of about 2 to 15% of the total weight of said adhesive coating, and wherein said pressure-sensitive adhesive-coating further comprises glyceryl monolaurate in an amount of weight of about 0.2 to 5% of the total weight of said adhesive coating, the relative amounts of said ethyl oleate and said glyceryl monolaurate further being such that said glyceryl monolaurate accentuates the penetration enhancement effect of said fatty acid ester.

25. An adhesive-coated sheet material according to claim 22, wherein nitroglycerin is present in an amount by weight of about 25 to 35% of the total weight of said adhesive coating.

26. An adhesive-coated sheet material according to claim 22, wherein said sheet material contains nitroglycerin in said adhesive coating in an amount providing about 5 to 25 mg nitroglycerin per 5 $cm^2$ of said sheet material.

27. An adhesive-coated sheet material according to claim 22, wherein said backing is occlusive.

28. An adhesive-coated sheet material according to claim 22, wherein said alkyl alcohol of said A monomer contains 6 to 10 carbon atoms.

29. An adhesive-coated sheet material according to claim 28, wherein said A monomer is present in an amount by weight of about 88 to 96 percent of the total weight of all monomers in said copolymer.

30. A process according to claim 28, wherein said flexible backing is substantially impermeable to nitroglycerin.

* * * * *

UNITED STATES PATENT AND TRADEMARK OFFICE
CERTIFICATE OF CORRECTION

PATENT NO. : 4,751,087
DATED      : June 14, 1988
INVENTOR(S) : S. M. Wick

It is certified that error appears in the above-identified patent and that said Letters Patent is hereby corrected as shown below:

| | |
|---|---|
| Col. 5, line 39 | "observed" should read --observed.-- |
| Col. 6, line 7 | "FIGURE" should read --figure-- |
| Col. 18, line 23 | "hear" should read --heart-- |
| Col. 19, line 32 | "alcohl" should read --alcohol-- |
| Col. 14, line 50 | "lāmaminating" should read --laminating-- |

Signed and Sealed this

Thirteenth Day of June, 1989

*Attest:*

DONALD J. QUIGG

*Attesting Officer*   *Commissioner of Patents and Trademarks*

REEXAMINATION CERTIFICATE (1938th)
United States Patent [19]
Wick

[11] B1 4,751,087

[45] Certificate Issued Mar. 2, 1993

[54] TRANSDERMAL NITROGLYCERIN DELIVERY SYSTEM

[75] Inventor: Steven M. Wick, Oakdale, Minn.

[73] Assignee: Riker Laboratories, Inc., St. Paul, Minn.

Reexamination Request:
No. 90/002,398, Aug. 9, 1991

Reexamination Certificate for:
Patent No.: 4,751,087
Issued: Jun. 14, 1988
Appl. No.: 725,215
Filed: Apr. 19, 1985

Certificate of Correction issued Jun. 13, 1989.

[51] Int. Cl.$^5$ ............ A61F 13/00; A61K 9/70; A61K 31/21
[52] U.S. Cl. ............ 424/449; 424/448; 514/509
[58] Field of Search ............ 424/449, 16, 21, 28, 424/32, 78, 81; 514/509; 604/896, 897

[56] References Cited
U.S. PATENT DOCUMENTS

4,420,470 12/1983 Otsuka et al. ............ 424/449
4,485,087 11/1984 Otsuka et al. ............ 424/449

FOREIGN PATENT DOCUMENTS

59-199628 11/1984 Japan.
1518683 7/1978 United Kingdom.

*Primary Examiner*—Nathan M. Nutter

[57] ABSTRACT

A pressure-sensitive adhesive tape for delivering nitroglycerin to skin, the tape comprising a backing with a layer of inert pressure-sensitive adhesive attached thereto, said pressure-sensitive adhesive layer comprising a pressure-sensitive adhesive polymer, skin penetration-enhancing ingredients and a relatively high concentration of nitroglycerin. The tape is useful for systemic treatment of angina pectoris, control of hypertension and treatment of congestive heart failure.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–30 is confirmed.

* * * * *